(12) United States Patent
Wang et al.

(10) Patent No.: US 10,405,793 B2
(45) Date of Patent: Sep. 10, 2019

(54) SYSTEMS AND METHODS FOR IN VIVO VISUALIZATION OF LYMPHATIC VESSELS WITH OPTICAL COHERENCE TOMOGRAPHY

(71) Applicant: University of Washington, Seattle, WA (US)

(72) Inventors: Ruikang K. Wang, Seattle, WA (US);
Siavash Yousefi, Seattle, WA (US);
Utku Baran, Seattle, WA (US)

(73) Assignee: University of Washington, Seattle, WA (US)

( * ) Notice: Subject to any disclaimer, the term of this patent is extended or adjusted under 35 U.S.C. 154(b) by 712 days.

(21) Appl. No.: 14/789,291

(22) Filed: Jul. 1, 2015

(65) Prior Publication Data
US 2016/0000368 A1    Jan. 7, 2016

Related U.S. Application Data
(60) Provisional application No. 62/019,790, filed on Jul. 1, 2014.

(51) Int. Cl.
*A61B 5/00*    (2006.01)
*A61B 5/026*    (2006.01)

(52) U.S. Cl.
CPC ............ *A61B 5/418* (2013.01); *A61B 5/0059* (2013.01); *A61B 5/0062* (2013.01);
(Continued)

(58) Field of Classification Search
CPC ..... A61B 5/418; A61B 5/0062; A61B 5/0073; A61B 5/0059; A61B 5/0066; A61B 5/725; A61B 5/0261
See application file for complete search history.

(56) References Cited

U.S. PATENT DOCUMENTS

| | | |
|---|---|---|
| 2014/0094689 A1 | 4/2014 | Cohen |
| 2014/0098099 A1 | 4/2014 | Welford |
| 2014/0100440 A1 | 4/2014 | Cheline |

FOREIGN PATENT DOCUMENTS

WO    2011097631 A2    8/2011

OTHER PUBLICATIONS

Yousefi, Siavash, Jia Qin, Zhongwei Zhi, and Ruikang K. Wang. "Label-free optical lymphangiography: development of an automatic segmentation method applied to optical coherence tomography to visualize lymphatic vessels using Hessian filters." Journal of biomedical optics 18, No. 8 (2013): 086004.*

(Continued)

*Primary Examiner* — Carolyn A Pehlke
(74) *Attorney, Agent, or Firm* — Perkins Coie LLP

(57) ABSTRACT

The present technology relates generally to systems and methods for in vivo visualization of lymphatic vessels. A system includes an optical coherence tomography (OCT) device and a computing device coupled to the OCT device configured to cause the OCT device to perform an OCT scan, generate image data in response to the OCT scan, and apply an eigendecomposition filter to the image data to produce processed image data. Alternatively or in addition, the computing device can compensate for scattering attenuation along an optical axis of the OCT scan in the image data set to generate compensated image data, enhance contrast of the compensated image data along a cross-section substantially orthogonal to the optical axis to generate contrast-enhanced image data, and identify at least one lymphatic vessel in the image data.

8 Claims, 5 Drawing Sheets

(52) U.S. Cl.
CPC .......... *A61B 5/0066* (2013.01); *A61B 5/0073* (2013.01); *A61B 5/725* (2013.01); *A61B 5/0261* (2013.01)

(56) References Cited

OTHER PUBLICATIONS

Baran, Utku, Yuandong Li, and Ruikang K. Wang. "In vivo tissue injury mapping using optical coherence tomography based methods." Applied optics 54, No. 21 (2015): 6448-6453. published online Jun. 26, 2015.*
Bagade, Sapana S., and Vijaya K. Shandilya. "Use of histogram equalization in image processing for image enhancement." International Journal of Software Engineering Research & Practices 1, No. 2 (2011): 6-10.*
Alitalo, et al., "Lymphangiogenesis in development and human disease", Insight Review, Dec. 2005.
An, et al., "Full Range Complex Spectral Domain Optical Coherence Tomography for Volumetric Imaging at 47,000 A Scans per second", National Institutes of Health, Author Manuscript, Aug. 1, 2010.
An, et al., "Ultrahigh sensitive optical microangiography for in vivo imaging of microcirculations within human skin tissue beds", Optical Society of America, 2010.
An, et al., "Using ultrahigh sensitive optical microangiography to achieve comprehensive depth resolved microvasulature mapping for human retina", Journal of Biomedical Optics, Oct. 2011.
Banerji, et al., "LYVE-1, a New Homologue of the CD44 Glycoprotein, Is a Lymph-specific Receptor for Hyaluronan", The Rockefeller University Press, The Journal of Cell Biology, Feb. 22, 1999, 789-801.
Barrett, et al., "Imaging of the lymphatic system: new horizons", Contrast Media & Molecular Imaging, 2006, 230-245.
Baum, et al., "Normal Cutaneous Wound Healing: Clinical Correlation with Cellular and Molecular Events", American Society for Dermatologic Surgery, Inc., 2005.
Choma, et al., "Sensitivity advantage of swept source and Fourier domain optical coherence tomography", Department of Biomedical Engineering, Duke University, Sep. 8, 2001.
Clement, et al., "Imaging the lymphatic system: possibilities and clinical applications", Eur Radiol, 2004.
Fercher, et al., "Optical coherence tomography—principles and applications", Institute of Medical Physics, University of Vienna, 2003, 239-303.
Fischer, et al., "Flow Velocity of Cutaneous Lymphatic Capillaries in Patients with Primary Lymphedema", Int. J. Microcirc, Dec. 30, 1996, 143-149.
Frangi, et al., "Multiscale Vessel Enhancement Filtering", Image Sciences Institute, Utrecht University Hospital, 1998.
Girard, et al., "Shadow Removal and Contrast Enhancement in Optical Coherence Tomography Images of the Human Optic Nerve Head", Quality Improvement of Optical Coherence Tomography Images, Sep. 2011.
Gurfinkel, et al., "Pharmacokinetics of ICG and HPPH-car for the Detection of Normal and Tumor Tissue Using Fluorescence, Near-infrared Reflectance Imaging: A Case Study", Photochemistry and Photobiology, 2000, 94-102.
Huang, et al., "Optical Coherence Tomography", Science, Author Manuscript, Nov. 22, 1991.
Jia, et al., "Optical microangiography provides an ability to monitor responses of cerebral microcirculation to hypoxia and hyperoxia in mice", Journal of Biomedical Optics, Sep. 2011.
Jung, et al., "Three-dimenstional optical imaging of microvascular networks within intact lymph node in vivo", Journal of Biomedical Optics, Sep. 2010.
Jung, et al., "Tracking Dynamic Microvascular Changes during Healing after Complete Biopsy Punch on the Mouse Pinna Using Optical Microangiography", Optical Microangiography Tracks Would Healing, Feb. 2013.
Kalchenko, et al., "In vivo characterization of tumor and tumor vascular network using multi-modal imaging approach", Journal of Biophotonics, 2011, 645-649.
Kalchenko, et al., "Label free in vivo laser speckle imaging of blood and lymph vessels", Journal of Biomedical Optics, May 2012.
Kinmonth, "Lymphangiography in Man. A method of Outlining Lympthatic Trunks at Operation", May 9, 1951.
Kuznetsov, et al., "Multimodal imaging of vascular network and blood microcirculation by optical diagnostic techniques", Quantum Electronics, 2011, 308-313.
Lardinois, et al., "Staging of Non-Small-Cell Lung Cancer with Integrated Positron-Emission Tomography and Computed Tomography", The New England Journal of Medicine, 2003.
Lee, et al. "Statistical intensity variation analysis for rapid volumetric imaging of capillary network flux", Biomedical Optics Express, Mar. 13, 2014.
Leitgeb, et al., "Performance of fourier domain vs. time domain optical coherence tomography", Department of Medical Physics, University of Vienna, Apr. 21, 2003.
Lesage et al. "A review of 3D vessel lumen segmentation techniques: Models, features and extraction schemes", Medical Image Analysis 13, 2009, 819-845.
Martinez-Corral, et al., "In vivo imaging of lymphatic vessels in development, wound healing, inflammation, and tumor metastasis", Spanish National Cancer Research Centre, Apr. 17, 2012.
McLaughlin, et al., "Imaging of Human Lymph Nodes Using Optical Coherence Tomography: Potential for Staging Cancer", American Association for Cancer Research, 2010.
McNeill, et al., "Whole-Body Lymphangioscintigraphy: Preferred Method for Initial Assessment of the Peripheral Lymphatic System", Musculoskeletal Radiology, 1989.
Mellor, et al., "J. Vasc. Res", Enhanced Cutaneous Lymphatic Network in the Forearms of Women with Postmastectomy Oedema, 2000, 501-512.
Misselwitz, "MR contrast agents in lymph node imaging", European Journal of Radiology, 2006, 375-382.
Oliver, et al., "Lymphatic Vaculature Development", Nature Review, Jan. 2004.
Partsch, et al., "The dermal lymphatics in lymphoedema visualized by indirect lymphography", British Journal of Dermatology, 1984.
Qin, et al., "In vivo volumetric imaging of microcirculation within human skin under psoriatic conditions using optical microangiography", National Institutes of Health, Author Manuscript, Feb. 2011.
Rockson, "The Lymphatic Continuum Revisited", New York Academy of Sciences, 2008.
Shaw, et al., "Wound repair at a glance", Cell Science at a Glance, 2009.
Suga, et al., "Visualization of Breast Lymphatic Pathways With an Indirect Computed Tomography Lymphography Using a Nonionic Monometric Contrast Medium Iopamidol", Investigative Radiology, 2003.
Suri, et al., "A Review on MR Vascular Image Processing Algorithms: Acquisition and Prefiltering: Part I", IEEE Transactions on Information Technology in Biomedicine, Dec. 2002.
Szuba, et al., "The Third Circulation: Radionuclide Lymphoscintigraphy in the Evaluation of Lymphedema", The Journal of Nuclear Medicine, Jan. 2003.
Tammela, et al., "Lymphangiogenesis: Molecular Mechanisms and Future Promise", Molecular/Cancer Biology Laboratory and Haartman Institute, Feb. 19, 2010.
Tomlins, et al., "Theory, developments and applications of optical coherence tomography", Institute of Physics Publishing, 2005, 2519-2535.
Vakoc: et al., "Three-dimenstional microscopy of the tumor microenvironment in vivo using optical frequency domain imaging", Nature America, Inc., 2009.
Wang, et al., "A practical approach to eliminate autocorrelation artefacts for volume-rate spectral domain optical coherence tomography", Institute of Physics Publishing. Physics in Medicine and Biology, 2006, 3231-3239.

(56) References Cited

OTHER PUBLICATIONS

Wang, et al., "Depth-resolved imaging of capillary networks in retina and choroid using ultrahigh sensitive optical microangiography", National Institutes of Health, Author Manuscript, May 1, 2010, 1467-1469.

Wang, et al., "In vivo full range complex Fourier domain optical coherence tomography", Applied Physics Letters, 2007.

Wang, et al., "Mapping of cerebro-vascular blood perfusion in mice with skin and skull intact by Optical Micro-AngioGraphy at 1.3m wavelength", Optical Society of America, 2007.

Wang, et al., "Three dimensional optical angiography", Optics Society of America, 2007.

Xu, et al., "Automatic detection of stent struts with thick neointimal growth in intravascular optical coherence tomography image sequences", Institute of Physics and Engineering in Medicine, 2011.

Yousefi, et al., "Eigendecomposition-Based Clutter Filtering Technique for Optical Micro-Angiography", National Institutes of Health, Author Manuscript, Aug. 2011.

Yuan, et al., "The role of radionuclide lymphoscintigraphy in extremity lymphedema", Annals of Nuclear Medicin, 2006, 341-344.

Zhi, et al., "Highly sensitive imaging of renal microcirculation in vivo using ultrahigh sensitive optical microangiography", Optical Society of America, 2011.

Zhi, et al., "Label-free 3D imaging of microstructure, blood and lymphatic vessels within tissue in vivo", Journal of Biomedical Optics, May 2012.

* cited by examiner

SYSTEMS AND METHODS FOR IN VIVO VISUALIZATION OF LYMPHATIC VESSELS WITH OPTICAL COHERENCE TOMOGRAPHY

CROSS-REFERENCE TO RELATED APPLICATION

This application claims the benefit of U.S. Provisional Patent Application No. 62/019,790, filed Jul. 1, 2014, which is incorporated herein by reference in its entirety.

TECHNICAL FIELD

The present technology is generally related to systems and methods for in vivo visualization of lymphatic vessels. In particular, several embodiments are directed to imaging lymphatic vessels using optical coherence tomography techniques.

BACKGROUND

The circulatory network in mammals is composed of a cardiovascular and lymphatic system responsible for delivering oxygen, nutrition, immune cells, and hormones to tissue and collecting waste materials from cells within living organs. These compounds are exchanged with cells via capillary beds where, due to the high blood pressure at arterioles, some part of plasma leaks into the interstitial space. After the exchange, the protein-rich interstitial fluid (lymph) is collected and returned back to the circulatory system by the lymphatic system. The lymphatic system consists of unidirectional, thin-walled capillaries, and a larger vessel network that drains lymph fluid from extracellular spaces within organs into larger collecting ducts. Finally, lymph is returned to venous circulation through the thoracic duct. The lymphatic system also includes lymphoid organs such as lymph nodes, tonsils, Peyer's patches, spleen, and thymus which play a crucial part in immune response. The lymphatic system usually develops in parallel to the blood vessels in the skin and in most internal organs and is not present in the central nervous system, bone marrow, and avascular structures such as cartilage, epidermis, and cornea. Besides draining lymph fluid from extracellular spaces, other roles of the lymphatic system include absorbing lipids from the intestinal tract, maintaining the fluid hemostasis and transporting antigen-presenting cells and leukocytes to lymphoid organs. Also, the lymphatic system plays an important role in the development of several diseases such as cancer, lymphedema, and some inflammatory conditions.

DETAILED DESCRIPTION

Overview

Figure 1A:
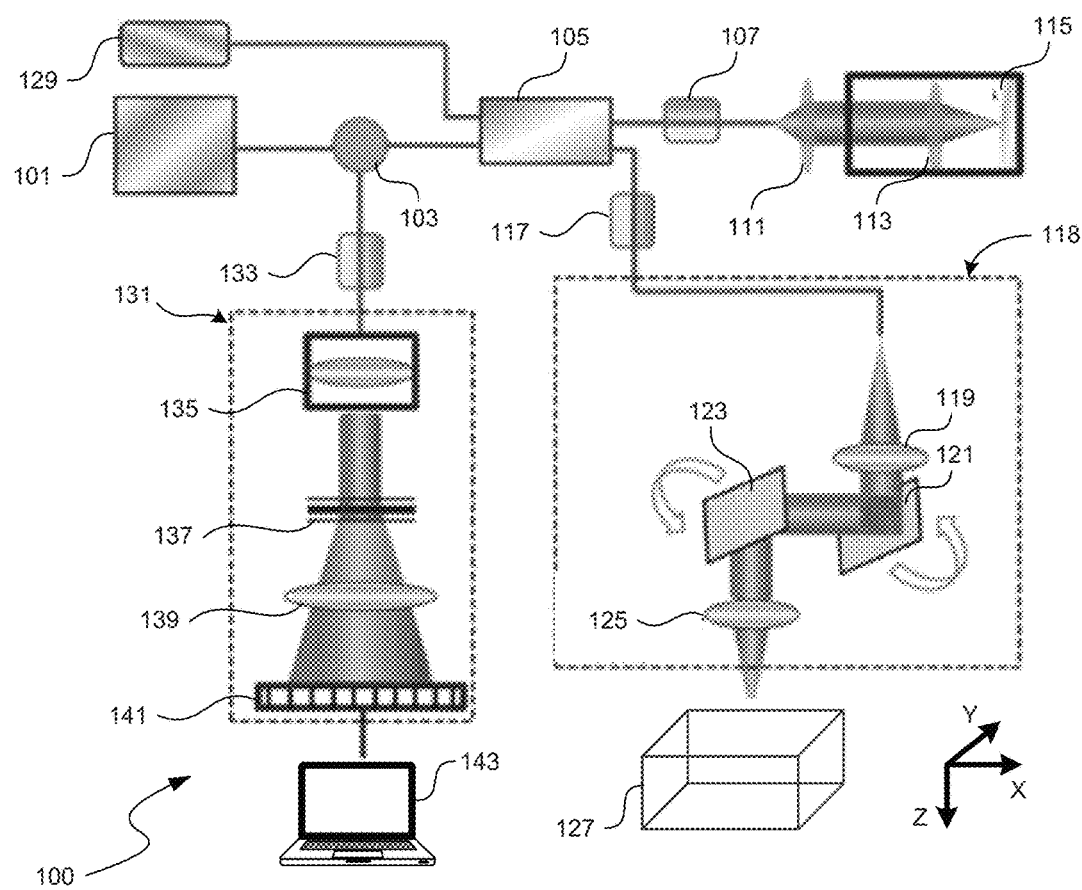
FIG. 1A is a schematic illustration of an optical coherence tomography (OCT) imaging and image-processing system configured in accordance with embodiments of the present technology.

The present technology is directed to systems and methods for visualizing lymphatic vessels using optical coherence tomography (OCT) techniques. As noted below, lymph fluid is clear and accordingly does not lend itself to conventional OCT imaging, which generally requires highly scattering samples. In one aspect of the present technology, an automatic filtering technique and vesselness model is used to detect lymphatic vessels via OCT images. For example, the vesselness model can be based on Hessian multi-scale filters for segmenting lymphatic vessels in OCT images. Hessian filters estimate tubular and vessel-like structures and the multiscale approach allowed segmenting vessels with different size. In another aspect of the present technology, the depth-based scattering attenuation is reduced by sequentially processing OCT cross-sections, followed by contrast enhancement along orthogonal cross-sections.

Although lymphatic vessels were first described in the early 17th century, they have been termed the "forgotten circulation" because their role and function was mostly ignored due to the lack of monitoring and imaging techniques. In recent years, several contrast-enhanced and labeled image modalities and imaging techniques including X-ray, computed tomography (CT), magnetic resonance imaging (MRI), ultrasound, and optical imaging have been used in clinical and animal studies for noninvasive and direct lymphatic imaging. In lymphangiography, for example, an iodinated contrast agent such as blue dye or Iopamidol is either injected directly into a lymphatic vessel or indirectly into intradermal area for X-ray or CT. Although CT scans differentiated iodine concentration and lymph node morphology in normal and malignant lymph node, their application was limited due to their fast drainage from blood vessels that limited the imaging time in clinic. More recent development of bismuth sulfide nanoparticles CT agents with longer circulating half-life addressed some of the problems while their long-term toxicity is a major concern. Lymphoscintigraphy with 99m-technetium (TC-99m) is the most common nuclear method of imaging the lymphatics that enables visualization of the lymphatic network using single-photon emission computer tomography (SPECT). However, this technique requires rejection of scattered gamma photons and a large number of photons remain undetected and scanning times can be long. In contrast, positron emission tomography with beta-emitting isotopes (18-F-fluro-2-deoxy-Dglucose, FDG) provides higher sensitivity specifically when combined with CT for better spatial resolution. MRI, unlike nuclear imaging techniques, does not require ionizing radiation exposure. MR lymphangiography is performed by intravenous or interstitial injection of gadolinium-labeled diethylene-triaminepentaacetic acid (Gd-DTPA), Gd dendrimetrs or liposomes and iron oxide particles. Fluorescence microlymphangiography is an optical imaging technique based on absorption of light in the visible or near-infrared (NIR) region by utilizing intradermal, subcutaneous, or intravenous injection of fluorescein contrast agents such as indocyanin-green (IC-Green) and fluorophore to map lymphatic vasculature. Also, molecular staining of lymph endothelium has been made possible by the discovery of lymph-specific molecular markers such as Prox-1, lymph endothelial-specific hyaluronan receptor 1 (LYVE-1), and vascular endothelial growth factor receptor 3 (Vegfr3) that were extensively used for imaging lymphatic vessels in development, wound healing, inflammation, and tumor metastasis.

OCT has been widely used to noninvasively provide high-resolution, depth-resolved cross sectional and three-dimensional (3-D) images of highly scattering samples, for example blood cells in microvasculature. Since the lymph fluid is clear and transparent, the lymph fluid is lowly scattering and therefore not conducive to conventional OCT imaging, in which lymphatic vessels appear as reduced scattering vessel-like areas in OCT structure cross section images. These low scattering transparent vessel-like structures have been verified as lymphatic vessels by injecting Evan's blue dye injection into the tissue and observing the uptake path by lymphatic vessels. These vessels can be visualized by applying a lower threshold on the intensity image. However, the intensity-threshold technique does not take the physical shape of the vessels into account. Also, it is not robust to intensity variations and noise caused by speckle and light absorption in the structure. These limitations increase the chances of segmentation error and false alarms in identifying lymphatic vessels. Accordingly, there is a need for improved systems and methods for in vivo, label-free imaging of lymphatic vessels.

Specific details of several embodiments of the present technology are described below with reference to FIGS. 1A-5. Although many of the embodiments are described below with respect to devices, systems, and methods for in vivo visualization of lymphatic vessels, other embodiments are within the scope of the present technology. Additionally, other embodiments of the present technology can have different configurations, components, and/or procedures than those described herein. For instance, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

Lymphatic Vessel Visualization Systems

FIG. 1A is a schematic illustration of an OCT imaging and image-processing system 100 configured in accordance with embodiments of the present technology. The system 100 operates as a Michelson interferometer in which light in a reference arm is compared with light reflected from a scattering sample. The system 100 comprises an infrared light source 101 and an optical circulator 103 positioned to couple the light from the infrared light source 101 into a fiber coupler 105. The infrared light source 101 comprises, for example, a superluminescent diode (SLD) with a center wavelength of about 1310 nm and a bandwidth of approximately 65 nm, delivering an axial resolution of approximately 12 microns in the air. In other embodiments, however, the infrared light source 101 may have a different configuration and/or features. The light output from the fiber coupler 105 passes through a polarization controller 107 before reaching lenses 111, 113 and a stationary mirror 115. Light reflected from the mirror 115 passes back through lenses 111, 113 and the polarization controller 107 and into the fiber coupler 105. This reflected light provides the reference arm of the fiber-based Michelson interferometer.

In the sample arm 118 of the interferometer, light is output from the fiber coupler 105 and passes through a polarization controller 117 before reaching a collimating lens 119, a y-scanner mirror 121, an x-scanner mirror 123, and objective lens 125 before reaching the sample 127. Light scatters and reflects within the sample 127, and propagates back into the fiber coupler 105.

The objective lens 125 can be, for example, a microscopy lens with 18-mm focal length, which can provide approximately 5.8 micron lateral resolution. Since the infrared light source 101 is invisible to the human eye, a visible light source 129 can be used as a guiding beam to locate the imaging position by coupling light from the visible light source 129 into the fiber coupler 105. In other embodiments, however, the objective lens 125 and/or visible light source 129 may have different configurations and/or features.

The fiber coupler 105 recombines the backscattered light from the sample 127 and the reflected light from the mirror 115. The system 100 routes the recombined light from the coupler 105 to a spectrometer 131 via the circulator 103 and another polarization controller 133. The spectrometer 129 includes a collimating lens 135, a grating 137 that separates the light by wavelength, a lens 139, and a CCD image sensor 141. Data from the CCD image sensor 141 is then output to a processing unit 143 for image processing and analysis.

In some embodiments, the CCD image sensor 141 can have a line scan rate of approximately 47,000 lines per second, and the spectral resolution can be approximately 0.141 nm, providing a detectable depth range of approximately 3.0 mm on either side of the zero-delay line. The scan area can be determined, at least in part, on the scanning of the y-scanner mirror 121 and the x-scanner mirror 123. During a scan, for example, the x-scanner 123 can scan more quickly and be driven with a sawtooth waveform, and the y-scanner can scan more slowly and be driven with a step function waveform. In conjunction, the fast and slow scans cover a rectangular area on the sample 127. In some embodiments, the sample 127 can be translated with respect to the system 100, for example via a mechanical stage or other suitable mechanism. Multiple separate images of the sample 127 can be stitched together or otherwise combined to create a larger composite image. In other embodiments, however, the CCD image sensor 141, y-scanner 121, and/or x-scanner 123 may have different configurations.

Figure 1B:
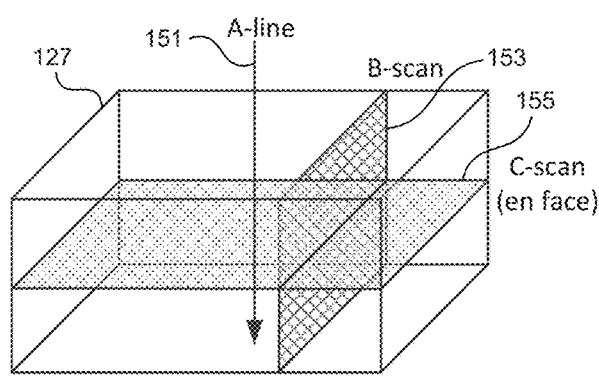
FIG. 1B is a schematic illustration of OCT image planes in a sample.

FIG. 1B is a schematic illustration of OCT image planes in the sample 127. Referring to FIGS. 1A and 1B together, the A-line 151 represents a single axial scan obtained with the system 100. A plurality of A-lines 151 are taken in succession over an area of the sample 127, for example, by scanning quickly with the x-scanner 123 and simultaneously scanning slowly with the y-scanner 121. Groups of A-lines 151 can then be combined to generate planar scans, for example, a group of A-lines 151 aligned along the y-axis at a particular position along the x-axis can be used to generate a B-scan 153, which is an OCT image along the y-z plane of the sample 127. A C-scan 155 is a cross-sectional view of the sample 127 along the x-y plane that is obtained from the OCT image data.

The system 100 of FIG. 1A is one example of an OCT imaging system, in particular a spatially encoded frequency domain OCT system (also known as a spectral domain or Fourier domain OCT). However, various other OCT imaging systems can be used in accordance with the present technology, for example, swept source OCT, time domain OCT, etc. The system 100 of FIG. 1A is also a single point (confocal) OCT system. In other embodiments, however, partial-field or full-field OCT systems can be used in accordance with the present technology.

The processing unit 143 can be a computing device that includes a suitable processor or central processing unit (CPU) that processes image data in accordance with computer-readable instructions stored on system memory. The CPU, for example, can control performance of the various routines described herein with reference to, for example, FIGS. 2 and 4. The CPU may be any logic processing unit, such as one or more CPUs, digital signal processors (DSPs), application-specific integrated circuits (ASICs), etc. The CPU may be a single processing unit or multiple processing units in a device or distributed across multiple devices. The CPU is connected to a memory and may be coupled to other hardware devices, for example, with the use of a bus (e.g., a PCI Express or Serial ATA bus). The CPU can include, by way of example, a standard personal computer ("PC") or other type of embedded computer running any suitable operating system, such as Linux, Windows, Android, iOS, MAC OS, or an embedded real-time operating system. In some embodiments, the CPU can be a small form factor PC with integrated hard disk drive ("HDD") or solid-state drive ("SSD") and universal serial bus ("USB") or other ports to communicate with the other components. In other embodiments, the CPU can include a microprocessor with a stand-alone motherboard that interfaces with a separate HDD. The memory can include read-only memory (ROM) and random access memory (RAM) or other storage devices, such as disk drives or SSDs, that store the executable applications, test software, databases and other software required to, for example, implement the various routines described herein. In some embodiments, the processing unit 143 can be connected via hardwired connection to the spectrometer 131, while in other embodiments the processing unit 143 can be remote from the spectrometer 131 and the system 100. For example, data from the spectrometer 131 can be captured and processed later at a remote location.

Methods for Visualizing Lymphatic Vessels Using Eigendecomposition Filters

Figure 2:
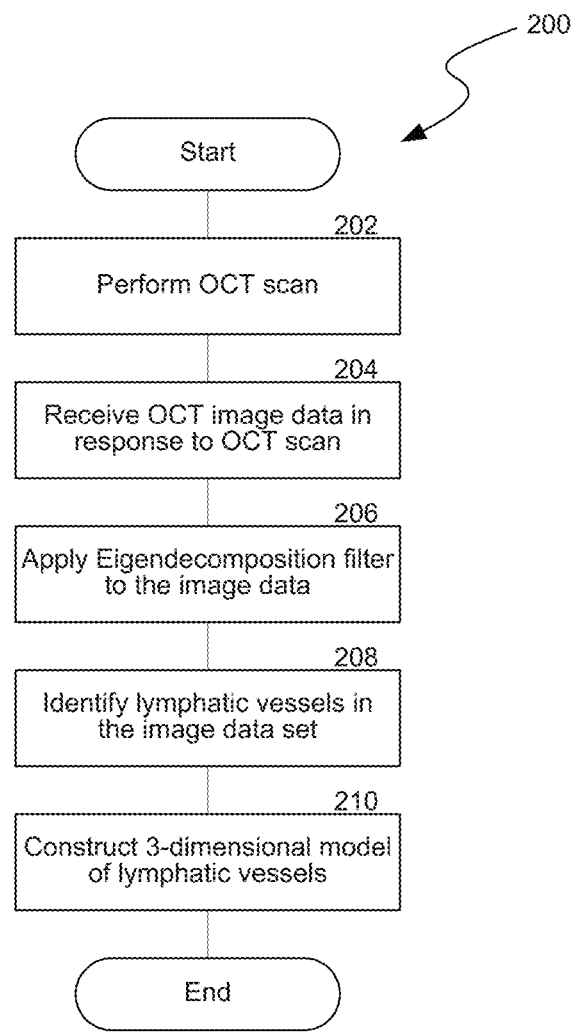
FIG. 2 is a flow diagram of a routine for visualizing lymphatic vessels using an eigendecomposition filter configured in accordance with embodiments of the present technology.

FIG. 2 is a flow diagram of a routine for visualizing lymphatic vessels using an eigendecomposition filter. The routine 200 begins in block 202 by performing an OCT scan of the sample. For example, the scan can be taken with an OCT device similar to the system 100 described above with respect to FIG. 1A or another suitable system. The sample can be a portion of a body that contains at least one lymphatic vessel. In block 204, the routine 200 receives OCT image data in response to the OCT scan. In some embodiments, the routine 200 can then pre-process the OCT image data, for example to remove shadows, enhance contrast, and/or to remove autocorrelation artifacts. The routine 200 can process repeated B-scans at the same spatial location to generate a cross-sectional blood flow perfusion map.

The routine 200 continues in block 206 by applying an eigendecomposition filter to the image data 206. In some embodiments, for example, the eigndecomposition filter can be a Hessian vesselness filter. One example of a Hessian vesselness filter is described below. The local behavior of an image I(x,s) at scale s and location x can be expressed by its Taylor series expansion up to second order given by:

$$I(x+\delta x, s) \approx I(x,s) + \delta x^T \nabla(I)_s + \delta x^T H(I)_s \delta x \qquad (1)$$

where $\nabla(.)_s$ and $H(.)_s$ are the gradient vector and Hessian matrix of the image at scale s, respectively. Since the volume cross-section images are discrete signals, finding their 2-D first-order and second-order derivatives can be ill-posed. Using the concepts of linear scale space theory, differentiation can be defined as a convolution with derivatives of a Gaussian:

$$\frac{\partial}{\partial x} I(x,s) = s^\gamma I(x,s) * \frac{\partial}{\partial x} G(x,s) \qquad (2)$$

where γ is the derivative normalization parameter, and $$G(x,s) = \frac{1}{\sqrt{2\pi s^2}} e^{\frac{-\|x\|^2}{2s^2}} \qquad (3)$$

and $\|.\|$ is the Euclidean norm operation. The second-order derivative can be expressed as:

$$\delta x^T H(I)_s \delta x = \left(\frac{\partial}{\partial x}\right)\left(\frac{\partial}{\partial x}\right) I(x,s) = s^{2\gamma} I(x,s) * \frac{\partial^2}{\partial x^2} G(x,s). \qquad (4)$$

By analyzing the eigenvalues and eigenvectors of the Hessian matrix, the principal direction of the local structure can be extracted, which is the direction of the smallest curvature (along the lymphatic vessel). By definition, the eigenvalues and vectors of the Hessian matrix are given by solving the following equations:

$$H_s e_{s,i} = \lambda_{s,i} e_{s,i} \qquad (5)$$

where $\lambda_{s,i}$ is the $i^{th}$ eigenvalue at scale s corresponding to normalized eigenvector $e_{s,i}$ and ($|\lambda_3| \leq |\lambda_2| \leq |\lambda_1|$) for a 3-D structure.

For an ideal tubular structure, the following conditions hold:

$$|\lambda_3| \approx 0 \qquad (6)$$

$$|\lambda_3| \ll |\lambda_2| \qquad (7)$$

$$\lambda_2 \approx \lambda_1 \qquad (8)$$

Based on the second-order ellipsoid, two geometric ratios are defined $$R_B = \frac{|\lambda_1|}{\sqrt{\lambda_2 \lambda_3}} \qquad (9)$$

$$R_A = \frac{|\lambda_2|}{|\lambda_3|} \qquad (10)$$

The first ratio ($R_B$) accounts for the deviation from a blob-like structure but cannot distinguish between a line-like and a plate-like pattern. The second ratio refers to the largest cross section area of the ellipsoid that can distinguish between plate-like and line-like structure as it is zero in the latter case.

In order to distinguish background noise where no structure is present, a Frobenius matrix norm can be utilized. This measure is derived from eigenvalues of the Hessian matrix by:

$$R_C = \|H\|_F = \sqrt{\sum_{j \leq D} \lambda_j^2} \quad (11)$$

where D is the dimension of the image. This measure will be low in the background where no structure is present and the eigenvalues are small for the lack of contrast. In regions with high contrast compared to the background, the norm will become larger since at least one of the eigenvalues will be large.

Accordingly, the vesselness function at scale s is defined as $$v_0(s) = \begin{cases} 0 \text{ if } \lambda_2 > 0 \text{ or } \lambda_3 > 0 \\ \left(1 - e^{-\frac{R_A^2}{2\alpha^2}}\right) * e^{-\frac{R_B^2}{2\beta^2}} * \left(1 - e^{-\frac{R_C^2}{2\theta^2}}\right) \end{cases} \quad (12)$$

where $\alpha$, $\beta$, and $\theta$ are thresholds which control the sensitivity of the function to the measures $R_A$, $R_B$, and $R_C$. This expression maps features into probability-like estimates of vesselness according to different criteria. In some embodiments, the values for thresholds $\alpha$, $\beta$, and $\theta$ can be between about 0.1 and 0.9, between about 1 and 20, and between about 100 and 1,000, respectively. Based on the selected threshold values, an example cut-off value for v(s) indicating vesselness can be approximately 0.2.

The vesselness measure can be analyzed at different scales. The response of the filter will be maximum at a scale that approximately matches the vessel size.

$$v_0(\gamma) = \operatorname{argmax}_s v_0(s,\gamma), \ s_{min} < s < s_{max} \quad (13)$$

where $s_{min}$ and $s_{max}$ are lower and upper bounds in the range of scale (vessel sizes). The selected values for $s_{min}$ and $s_{max}$ can vary depending on the size of the vessels to be segmented. For example, for relatively small vessels, $s_{min}$ can be about 0.1 mm and $s_{max}$ can be approximately 5 mm, with the scale evaluated at 0.1 mm increments between $s_{min}$ and $s_{max}$. For larger vessels, $s_{min}$ can be approximately 0.5 mm, and $s_{max}$ can be approximately 15 mm, with the scale evaluated at 0.5 mm increments between $s_{min}$ and $s_{max}$.

A similar vesselness function for 2-D images (cross section) follows directly from the same reasoning as the 3-D vesselness function above, and is given by:

$$v_0(s) = \begin{cases} 0 \text{ if } \lambda_2 > 0 \\ e^{-\frac{R_B^2}{2\beta^2}} * \left(1 - e^{-\frac{R_C^2}{2\theta^2}}\right) \end{cases} \quad (14)$$

where $$R_B = \frac{\lambda_1}{\lambda_2} \quad (15)$$

The OCT image data can be processed according to the vesselness functions shown above, using either the three-dimensional vesselness function (equation 12) if three-dimensional OCT image data is used, or else successive cross section OCT image data can be processed according to the two-dimensional function (equation 14). Based on the vesselness functions, the lymphatic vessels are identified and segmented in block 208. For example, the output of the vesselness function can provide a probability-like estimate of which pixels or voxels constitute part of lymphatic vessels. By applying a threshold probability above which pixels or voxels are deemed to be part of a lymphatic vessel, the lymphatic vessels can be identified and segmented. Next, the routine 200 continues in block 210 by constructing a three-dimensional model of the lymphatic vessels. In the case of two-dimensional analysis of cross-sections, adjacent cross-sections can be visualized in volumetric formation to generate a three-dimensional vessel map.

Once the lymphatic vessels have been identified and visualized, they may be quantified or otherwise further analyzed. For example, the three-dimensional vessel map can be used to calculate the lymphatic vessel area density (LVAD), defined as the area of the segmented lymphatic vessels divided by the total area of the imaged sample. Lymphatic vessel diameter (LVD) can also be quantified, for example using Euclidean distance transform (EDT) of the binarized lymphatic vessel C-scan projection map. The EDT of each pixel in a binary image measures the Euclidean distance between that pixel and the nearest nonzero pixel element of that image. First, the lymphatic vessel map can be binarized above a threshold. Then, the vessel centerline can be extracted by skeletonizing the binary vessel map. Finally, the distance transform of the intensity-inverted lymphatic vessel map can be estimated at each vessel centerline pixel. Using EDT at the vessel centerline therefore provides an estimate of the vessel diameter.

Figure 3A:
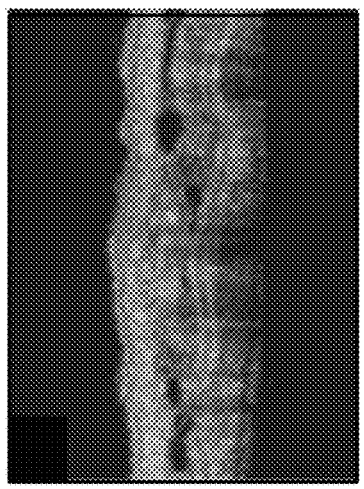
FIG. 3A is an OCT B-scan cross-section of blood vessels.
Figure 3B:
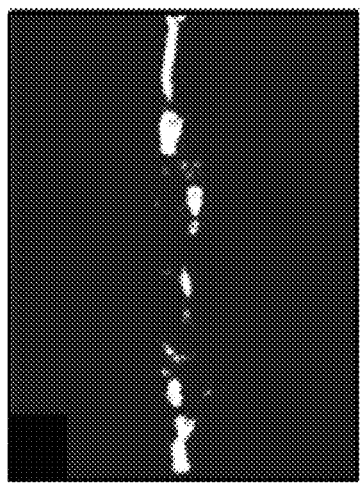
FIG. 3B is an OCT B-scan cross-section of lymphatic vessels.
Figure 3C:
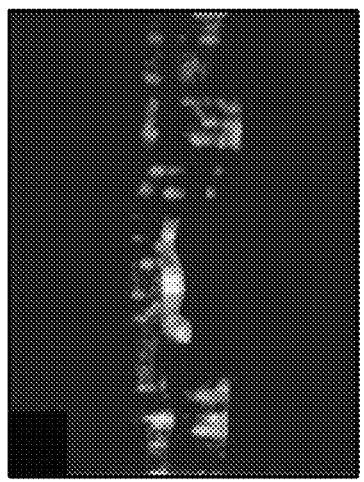
FIG. 3C is an OCT B-scan cross-section of combined blood and lymphatic vessels.

FIGS. 3A-3C illustrate example B-scans of OCT data. Specifically, FIG. 3A illustrates a B-scan (i.e., cross-section along the y-z plane, FIG. 1B) of blood vessels, FIG. 3B illustrates a B-scan of lymphatic vessels, and FIG. 3C shows the full OCT B-scan image from which FIGS. 3A and 3B are derived. As described above, a plurality of such B-scans can be processed and then combined to generate three-dimensional volumetric data.

Figure 3D:
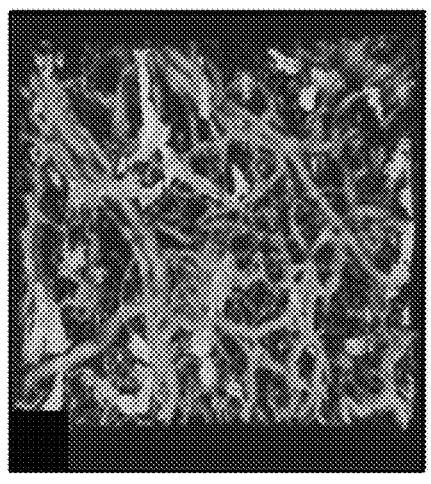
FIG. 3D is a three-dimensional volume rendering of blood vessels.
Figure 3E:
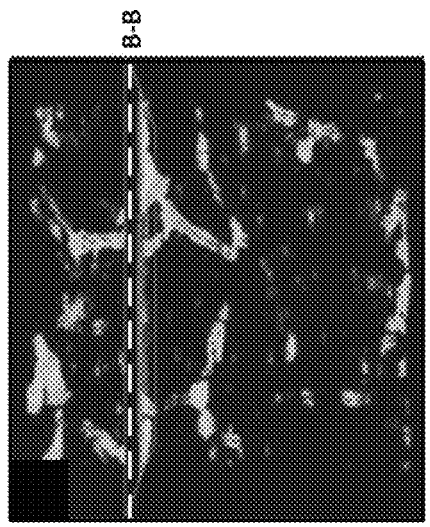
FIG. 3E is a three-dimensional volume rendering of lymphatic vessels.
Figure 3F:
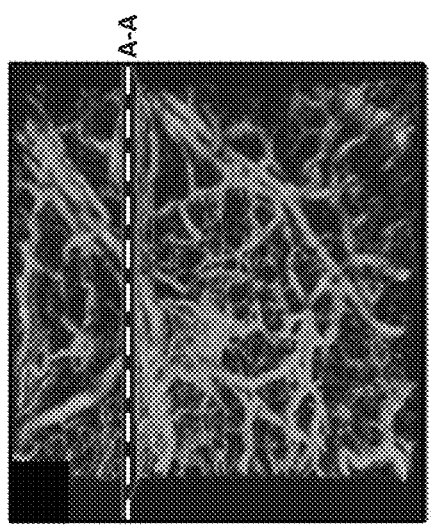
FIG. 3F is a three-dimensional volume rendering of combined blood and lymphatic vessels.

FIGS. 3D-3F, for example, illustrate example processed three-dimensional volume renderings. Specifically, FIG. 3D illustrates a three-dimensional volume rendering of blood vessels. The plane A-A is shown along which the B-scan of FIG. 3A is taken. FIG. 3E illustrates a three-dimensional volume rendering of lymphatic vessels, and shows the plane B-B alone which the B-scan of FIG. 3B is taken. FIG. 3F shows a combined three-dimensional volumetric rendering of the blood and lymphatic vessels, showing the three-dimensional complications of the circulatory system.

The eigendecomposition-filter technique described above (e.g., using a Hessian vesselness filter) allows segmenting vessels with different sizes. The use of this segmentation technique allows noninvasive, concurrent visualization of blood and lymphatic vessels in vivo as shown in FIG. 3E. In comparison with existing methods based on intensity thresholds, Hessian filters are more robust to the noise and intensity variations in the OCT structure image. Also, Hes-

Figure 4:
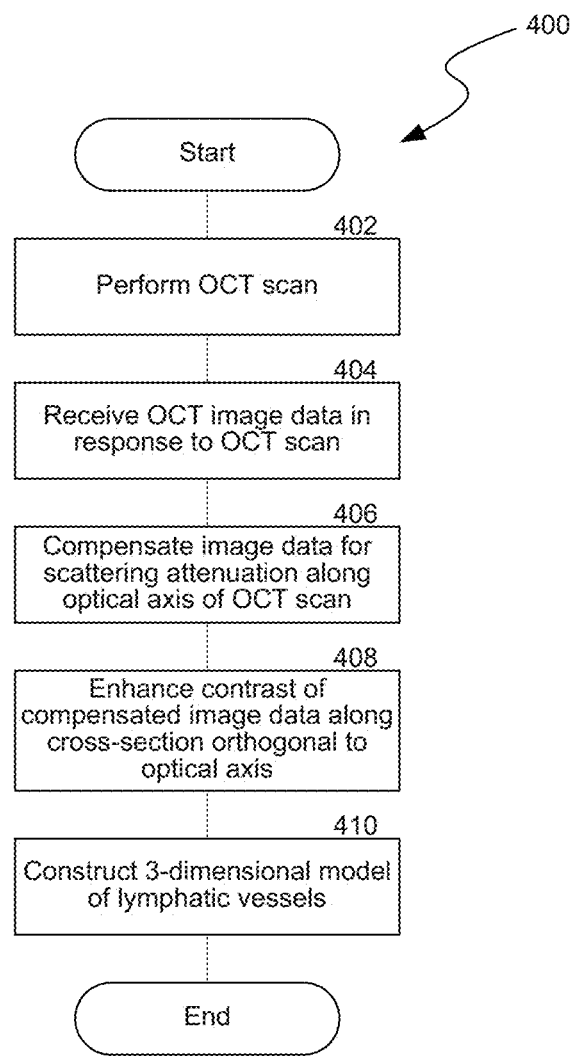
FIG. 4 is a flow diagram of a routine for visualizing lymphatic vessels using attenuation compensation and contrast enhancement configured in accordance with embodiments of the present technology.
Figure 5:
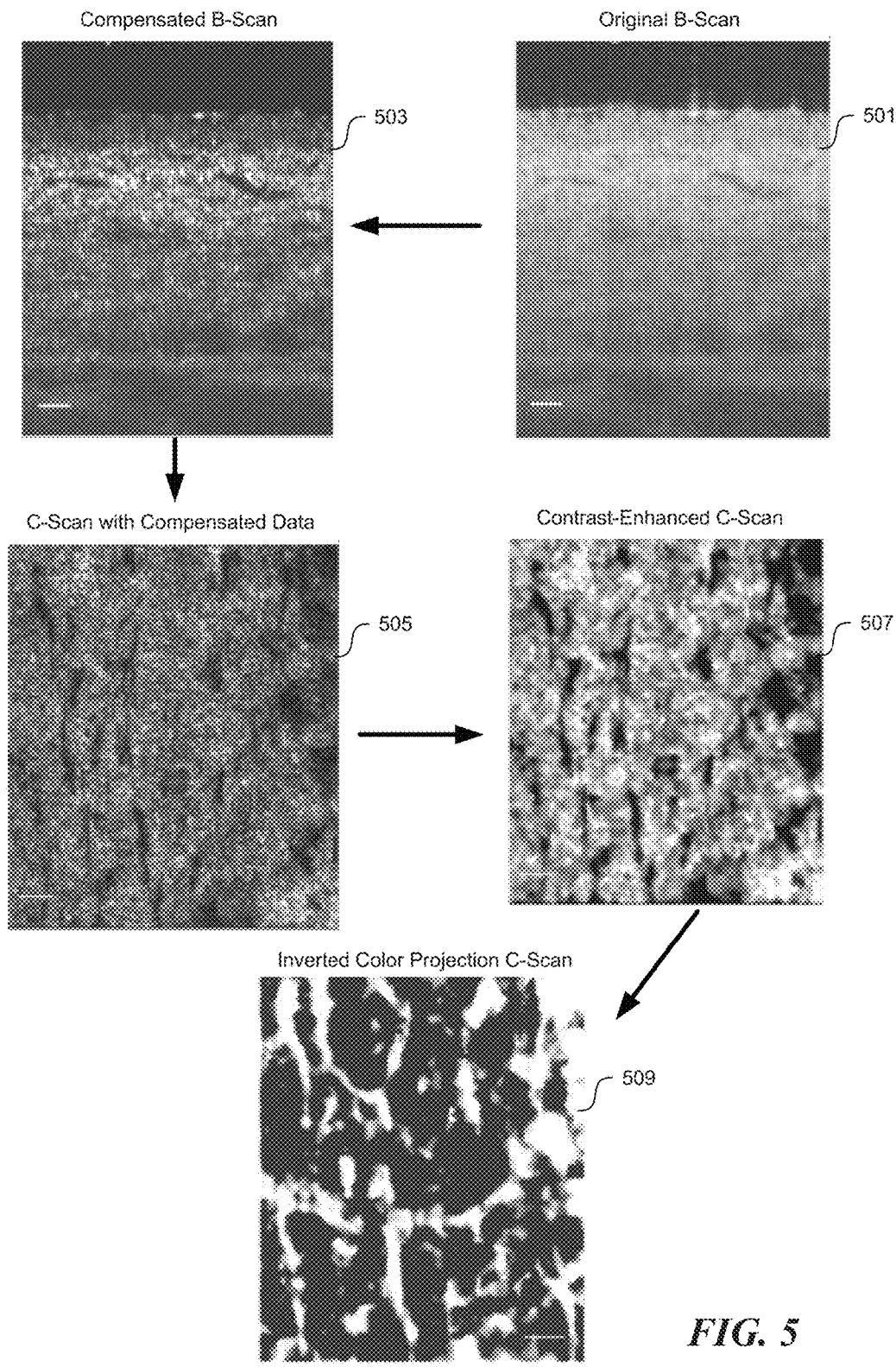
FIG. 5 illustrates a series of OCT images during processing according to the routine of FIG. 4.

Methods for Visualizing Lymphatic Vessels Using Scattering Attenuation Compensation FIG. 4 is a flow diagram of a routine 400 for visualizing lymphatic vessels using scattering attenuation compensation and contrast enhancement, and FIG. 5 illustrates a series of OCT images during processing according to the routine of FIG. 4. Referring to FIGS. 4 and 5 together, the routine 400 begins in block 402 by performing an OCT scan of the sample. For example, the scan can be taken with an OCT device similar to the system 100 described above with respect to FIG. 1A or other suitable system, or by using a swept-source OCT or other similar device. The sample can be a portion of a body that contains at least one lymphatic vessel. In block 404, the routine 400 receives OCT image data in response to the OCT scan. In some embodiments, the routine 400 can then pre-process the OCT image data, for example to remove shadows and/or to remove autocorrelation artifacts. The routine 400 can process repeated B-scans at the same spatial location and generating a cross-sectional blood flow perfusion map. An example B-scan at this stage is shown in FIG. 5 as the original B-scan 501.

The routine 400 continues in block 406 by compensating image data for scattering attenuation along the optical axis of the OCT scan (e.g., along an A-line scan as shown in FIG. 1B). For example, non-uniform intensity distribution of the OCT images due to light attenuation and heterogeneous tissue properties can make it difficult to increase the contrast and suppress the noise. In order to mitigate this problem, OCT structural images can be made uniform in axial and lateral directions using the methods described herein.

In a standard OCT system, for example swept-source OCT, the photodetector output I of the interference between a light beam reflected from a reference mirror and that from a sample can be described by the following equation:

$$I[k_m] = \frac{1}{2}\rho S[k_m]\left(R_R + R_S + 2\sqrt{R_R R_S}\cos(2k_m \Delta x)\right) \quad (16)$$

where k is the optical wavenumber, $\rho$ is the detector responsivity, $S[k_m]$ is the source spectral density, $\Delta x$ is the pathlength difference between the reference and the sample arms, and $R_R$ and $R_S$ are the reflectivity of the reference and the sample arm, respectively. The acquired signal ideally has values at M evenly spaced wavenumbers, so $k = \{k_1, k_2, \ldots, k_M\}$. The cross correlation term $H[k_m]$ is derived after removing the constant offset terms:

$$H[k_m] = \frac{1}{2}\rho S[k_m]\sqrt{R_R R_S}\cos(2k_m \Delta x) \quad (17)$$

Through a discrete inverse Fourier transform, an OCT A-line scan as a function of depth, z can be obtained:

$$D[z] = \Sigma_{k=1}^{M} H[k_m] e^{-2k_m z} \quad (18)$$

However, when light penetrates the tissue along the optical axis (e.g., the z-axis in FIG. 1B), it attenuates through the absorption ($\mu_a$) and scattering ($\mu_s$). This causes change in the acquired OCT A-line signal by modifying the previous equation in its continuous form:

$$D_A(z) = D(z) e^{-2\alpha \int_{z=d}^{\infty} D(u) du} \quad (19)$$

where $\alpha$ is the backscattering coefficient. When $\mu_z$ is large at a certain depth, such as at a blood vessel, it shadows the remaining points in that A-line, $D_A$. This effect contributes to the poor contrast between the tissue and the lymphatic vessels in the deeper sections. To compensate for the attenuation in the OCT images, this additional term can be removed by using the following operation:

$$\int_{z=d}^{\infty} D_A(z) = \int_{z=d}^{\infty} D(z) e^{-2\alpha \int_0^z D(u) du} \quad (20)$$
$$= \frac{e^{-2\alpha \int_0^z D(u) du}}{2\alpha} \rightarrow e^{-2\alpha \int_0^z D(u) du}$$
$$= 2\alpha \int_{z=d}^{\infty} D_A(z)$$

Substituting equation 20 into equation 19 and discretizing yields:

$$D[z] = \frac{D_A[z]}{2\alpha \int_{z=d}^{\infty} D_A[z]} \approx \frac{D_A[z]}{2\alpha \sum_{z=d}^{F} D_A[z]} \quad (21)$$

The backscattering coefficient $\alpha$ can be adjusted depending upon tissue characteristics. The value of the backscattering coefficient $\alpha$ depends on wavelength and particle size. In some embodiments, for example, the value of $\alpha$ for biological tissue for wavelengths between 400-1200 nm can be between about 0 and 1. F is the final pixel number in the A-line where most of the light is attenuated. Nevertheless, $D[z]$ in equation 21 is the compensated reflection that allows the display of compensated images having increased uniformity. This method assumes that the most of the light is attenuated within the recorded imaging depth range, and the backscattering coefficient is constant. Accordingly, equation 21 can be used to compensate the B-scan for scattering attenuation with depth along individual A-line scans. An example compensated B-scan is shown as image 503 in FIG. 5.

Due to the non-uniform mineral oil distribution and the non-flat surface of the skin, the OCT image intensity may also be non-uniform in C-scan (i.e., en face, see FIG. 1B) cross sections. This situation is generally more severe when a large field of view is used (e.g., greater than 2 mm²) Hence, an additional OCT image contrast enhancement step can be beneficial before mapping the lymphatic vessels. For example, a C-scan cross-section can be generated using the compensated B-scan data from block 406. An example compensated C-scan is shown as image 505 in FIG. 5. The routine 400 can then process then continue in block 408 by enhancing the contrast of the compensated image data along a cross-section orthogonal to the optical axis (e.g., by enhancing the contrast of the compensated C-scan).

One contrast enhancement technique involves histogram equalization. A histogram of an image is the probability distribution function of the occurrence of one specific gray level in that image. Histogram equalization is a contrast enhancement technique that increases the global contrast of images when the information content is represented by close contrast values. The histogram equalization method maps input intensities to an output image where its probability distribution function is uniform and its cumulative distribution function histogram is the same as the input image. This allows for stretching the contrast of the image to be distributed uniformly in the dynamic range. However, it may produce unrealistic images and amplify background noise while decreasing the usable data. Histogram equalization has been generalized to local histogram equalization which divides the input image into smaller regions and applies a histogram equalization algorithm to create a uniform distribution in each region. Unfortunately, it may also create noise amplification in homogenous regions.

To solve this problem, high peaks in the histograms, which correspond to homogenous regions in the image, can be clipped and the probability distribution function can be non-uniformly reconstituted with Rayleigh distribution to enhance the foreground and suppress the noise using the following equation:

$$y = y_{min} + \sqrt{2\beta^2 \ln\left(\frac{1}{1 - P_{input}(x)}\right)} \quad (22)$$

Here, y is the output intensity, x is the input intensity, $y_{min}$ is the low bound, $\beta$ is the Rayleigh parameter and $P_{input}(x)$ is the cumulative probability of the input image. A higher $\beta$ value will result in more contrast enhancement in the image while at the same time increasing saturation and noise levels. In some embodiments, the Rayleigh parameter $\beta$ can have a value of approximately 0.45. This technique transforms non-uniform, low-contrast OCT images into more uniform, high-contrast images which become useful in the mapping of the dark areas (e.g., lymphatic vessels) in the OCT images to a final C-scan (i.e., en face) image. To implement this technique, one can use the adapthisteq function in MATLAB®, for example. An example of a C-scan image with contrast enhancement is shown as image 507 in FIG. 5.

After enhancing contrast of the C-scan image, the routine 400 continues in block 410 by constructing a three-dimensional model of the lymphatic vessels. In one embodiment, constructing the model can include segmenting out the dermis layer, as the dermis scatters light more highly than the lymph and accordingly generates bright portions of the OCT image along each A-line scan. In order to segment out the dermis, the first layer of epidermis can be detected by extracting the first peak of each A-line. Then, the epidermal layer can be removed from the A-line scan, starting at this first identified peak until the dermal-epidermal junction is reached by using a pre-determined number of pixels (corresponding to the known or estimated thickness of the dermis layer). Finally, the pre-determined pixels corresponding to the papillary and reticular dermal layers in each A-line can be separated and stored. Repeating this procedure for every A-line flattens the curvature in the initial volume, and the interested volume can be automatically segmented accurately without the use of additional processing.

After segmenting out dermis, the pixels in each A-line can be sorted in ascending order, based on their intensities. Then, the first N number of pixels with minimum intensities are averaged before mapping on to a C-scan (en face) 2D plane. In summary, $Z_{en\_face}[x, y]$ is calculated as:

$$Z_{en\_face}[x, y] = \frac{\sum_{i=1}^{M} Z_{sorted}[x, y, i]}{M} \quad (23)$$

Here, $Z_{sorted}[x,y,i]$ is the value of the $i^{th}$ pixel in ascending order and M is the number of averaged pixels. This method is referred to herein as sorted minimum intensity projection (sMIP). A final C-scan (en face) image is produced in inverted colors, an example of which is shown as image 509 in FIG. 5.

Once the lymphatic vessels have been identified and visualized, they may be quantified or otherwise further analyzed. For example, the 3-D vessel map can be used to calculate the lymphatic vessel area density (LVAD) and the lymphatic vessel diameter (LVD) as described above. The techniques described above offer a way to quickly visualize the microvasculature and the lymphatic response to stimulation, non-invasively and without the need for exogenous contrast agents. These techniques can be used to image functional and constitutional changes through lymphangiogenesis and angiogenesis, providing opportunities to better understand tissue response to some pathological cases such as inflammatory diseases and cancer, and consequently facilitating new treatment options targeting the lymphatic system.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

In some embodiments, the use of an eigendecomposition filter and vesselness function can be combined with the scattering attenuation compensation techniques described above. For example, OCT image data can be processed to compensate for scattering attenuation along the optical axis, and C-scans can then be contrast-enhanced using histogram equalization. The compensated and contrast-enhanced image data can then be filtered via an eigendecomposition filter (e.g., a Hessian filter) and a vesselness function can be used to identify lymphatic vessels in the OCT image data.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system, comprising:
an optical coherence tomography (OCT) device;
a processor coupled to the OCT device;
a computer-readable medium storing instructions that, when executed by the processor, cause the processor to perform operations, the operations comprising:
    initiating an OCT scan with the OCT device, wherein the OCT scan includes a portion of the body containing at least one lymphatic vessel;
    generating an image data set in response to the OCT scan, wherein the image data set comprises a plurality of A-line scans parallel to the optical axis;
    processing each A-line scan by sorting pixels in the A-line scan in ascending order of intensity and averaging a first predetermined number of pixels with lowest intensity;
    generating compensated image data by compensating for scattering attenuation along an optical axis of the OCT scan in the image data set;
    generating contrast-enhanced image data by enhancing contrast of the compensated image data along a cross-section substantially orthogonal to the optical axis;
    segmenting out a dermis layer from the contrast-enhanced image data; and
    identifying at least one lymphatic vessel in the contrast-enhanced image data based, at least in part, on the contrast-enhanced image data; and
a display coupled to the processor and configured to display the contrast-enhanced image data.

2. The system of claim 1 wherein the operations further comprise identifying a three-dimensional map of the lymphatic vessel.

3. A method of visualizing lymphatic vessels in a body of a subject, the method comprising:
generating an optical coherence image data set in response to an optical coherence tomography (OCT) scan of a portion of the body containing at least one lymphatic vessel, wherein the image data set comprises a plurality of A-line scans parallel to the optical axis;
processing each A-line scan by sorting pixels in the A-line scan in ascending order of intensity and averaging a first predetermined number of the pixels with lowest intensity;
generating compensated image data by compensating for scattering attenuation along an optical axis of the OCT scan in the image data set;
generating contrast-enhanced image data by enhancing contrast of the compensated image data along a cross-section substantially orthogonal to the optical axis;
segmenting out a dermis layer from the contrast-enhanced image data; and
identifying at least one lymphatic vessel in the contrast-enhanced image data based, at least in part, on the contrast-enhanced image data.

4. The method of claim 3 wherein enhancing contrast comprises histogram equalization of the compensated image data.

5. The method of claim 3, further comprising creating a C-scan from the processed A-line scans.

6. The method of claim 3 wherein the C-scan is calculated as $$Z_{C\text{-}scan}[x, y] = \frac{\sum_{i=1}^{M} Z_{sorted}[x, y, i]}{M}$$

where, $Z_{sorted}[x,y,i]$ is the value of the $i^{th}$ pixel in ascending order and M is the number of averaged pixels.

7. The method of claim 5, further comprising displaying the C-scan with inverted pixel values.

8. The method of claim 5, further comprising combining a plurality of C-scans to create a three-dimensional image.

* * * * *